US008883128B2

(12) United States Patent
Bui et al.

(10) Patent No.: US 8,883,128 B2
(45) Date of Patent: *Nov. 11, 2014

(54) COSMETIC COMPOSITIONS CONTAINING A PROPYLPHENYLSILSESQUIOXANE RESIN AND A COSMETICALLY-ACCEPTABLE AROMATIC SOLVENT

(75) Inventors: Hy Si Bui, Piscataway, NJ (US); Mohamed Kanji, Edison, NJ (US)

(73) Assignee: L'Oréal (FR)

( * ) Notice: Subject to any disclaimer, the term of this patent is extended or adjusted under 35 U.S.C. 154(b) by 1670 days.

This patent is subject to a terminal disclaimer.

(21) Appl. No.: 12/131,253

(22) Filed: Jun. 2, 2008

(65) Prior Publication Data

US 2008/0305062 A1 Dec. 11, 2008

Related U.S. Application Data

(60) Provisional application No. 60/942,352, filed on Jun. 6, 2007.

(51) Int. Cl.
*A61Q 1/04* (2006.01)
*A61K 8/89* (2006.01)
*A61K 8/58* (2006.01)

(52) U.S. Cl.
CPC .. *A61Q 1/04* (2013.01); *A61K 8/585* (2013.01)
USPC ............................................. 424/64; 424/401

(58) Field of Classification Search
CPC .................................. A61K 8/585; A61Q 1/04
USPC ........................................ 424/401, 64, 78.08
See application file for complete search history.

(56) References Cited

U.S. PATENT DOCUMENTS

| | | | |
|---|---|---|---|
| 5,492,945 A | 2/1996 | Morita et al. | |
| 5,538,793 A | 7/1996 | Inokuchi et al. | |
| 5,756,568 A | 5/1998 | Morita et al. | |
| 5,783,657 A | 7/1998 | Pavlin et al. | |
| 5,945,471 A | 8/1999 | Morita et al. | |
| 6,268,466 B1 | 7/2001 | MacQueen et al. | |
| 6,280,748 B1 | 8/2001 | Morita et al. | |
| 6,376,078 B1* | 4/2002 | Inokuchi ...................... 428/403 | |
| 6,402,408 B1 | 6/2002 | Ferrari | |
| 6,517,818 B1 | 2/2003 | Golz-Berner et al. | |
| 6,552,160 B2 | 4/2003 | Pavlin | |
| 6,780,422 B2* | 8/2004 | Brieva et al. ................. 424/401 | |
| 6,936,242 B2* | 8/2005 | Elliott et al. ..................... 424/65 | |
| 7,127,280 B2 | 10/2006 | Dauga | |
| 2003/0077240 A1 | 4/2003 | LeGrow et al. | |
| 2004/0156806 A1 | 8/2004 | Patil et al. | |
| 2004/0180011 A1 | 9/2004 | Schlosser | |
| 2004/0234612 A1* | 11/2004 | Blin et al. ..................... 424/489 | |
| 2005/0180931 A1 | 8/2005 | Oguchi et al. | |
| 2005/0220728 A1 | 10/2005 | Kanji et al. | |
| 2006/0013839 A1 | 1/2006 | Yu | |
| 2006/0110347 A1* | 5/2006 | Lu et al. ....................... 424/70.1 | |
| 2006/0120983 A1 | 6/2006 | Blin et al. | |
| 2006/0292096 A1 | 12/2006 | Yu | |
| 2007/0093619 A1 | 4/2007 | Bui et al. | |
| 2007/0142521 A1 | 6/2007 | Brahms et al. | |
| 2007/0149703 A1 | 6/2007 | Caprasse et al. | |
| 2008/0152678 A1* | 6/2008 | Shah et al. ..................... 424/401 | |
| 2008/0305061 A1 | 12/2008 | Bui et al. | |
| 2008/0305062 A1 | 12/2008 | Bui et al. | |
| 2008/0305064 A1 | 12/2008 | Bui et al. | |
| 2008/0305067 A1 | 12/2008 | Bui et al. | |

FOREIGN PATENT DOCUMENTS

| | | | | |
|---|---|---|---|---|
| CN | 1823711 A | 8/2006 | | |
| EP | 0848029 A2 | 6/1998 | | |
| EP | 0963751 A2 | 12/1999 | | |
| JP | 06-011684 | 1/1994 | | |
| JP | 10-176059 | 6/1998 | | |
| JP | 2000063225 A | 2/2000 | | |
| JP | 2006-526019 A | 11/2006 | | |
| JP | 2010-513540 A | 4/2010 | | |
| JP | 2010-513541 A | 4/2010 | | |
| WO | 2004103323 A1 | 12/2004 | | |
| WO | 2005090444 A1 | 9/2005 | | |
| WO | WO 2005/090444 | 9/2005 | | |
| WO | 2005100444 A1 | 10/2005 | | |
| WO | WO2005100444 | * 10/2005 | ............. | C08G 77/04 |
| WO | 2005105031 A1 | 11/2005 | | |
| WO | 2008079478 A1 | 7/2008 | | |
| WO | 2008079479 A2 | 7/2008 | | |

OTHER PUBLICATIONS

"Diisostearyl fumarate," http://www.chemnet.com/Global/Products/diisostearylfumarate/Suppliers-0-0.html, Accessed Jul. 14, 2011.*

"Mineral Oil (Medium and Low Viscosity)," http://www.fao.org/ag/agn/jecfa-additives/specs/Monograph1/Additive-283.pdf, Accessed Jul. 14, 2011.*

"Sucrose acetate isobutyrate," pubchem, NCBI, accessed Oct. 1, 2013, pp. 1-5.*

Arndt Schlosser and Bryan Fry, Resins: The other kind of silicones, Wacker Silicones, Wacker Chemical Corp., Adrian, Michigan, USA, pp. 71-76, vol. 118, Aug. 8, 2003, 2003 Allured Publishing Corp., Cosmetic&Toiletries magazine.

International Cosmetic Ingredient Dictionary and Handbook, 9th edition, 2002, pp. 2903-2906, published by The Cosmetic, Toiletry, and Frangrance Association, 1101 17th Street, NW, Suite 300, Washington, DC 20036.

Kirk-Othmer, Encyclopedia of Chemical Technology, vol. 22, pp. 333-432, 3rd edition, 1979, A Wiley-Interscience publication, John Wiley and Sons.

(Continued)

*Primary Examiner* — Daniel Sullivan
*Assistant Examiner* — Rachael E Bredefeld
(74) *Attorney, Agent, or Firm* — Lerner, David, Littenberg, Krumholz & Mentlik, LLP

(57) ABSTRACT

The present invention is directed to a cosmetic composition containing: (a) at least one propylphenylsilsesquioxane resin; (b) at least one cosmetically-acceptable aromatic solvent; (c) at least one colorant, and (d) optionally, at least one cosolvent, and wherein the composition is substantially free of volatile solvents. Also disclosed is a method of imparting lasting shine onto lips by contacting the lips with the above described composition.

28 Claims, No Drawings

(56) References Cited

OTHER PUBLICATIONS

Wacker Silicones Wacker-Belsil SPR 45 VP Phenyl Propyl Polysilsesquioxane, Version 2.10, Jul. 13, 2004.
CTFA Dictionary, International Cosmetic Ingredient Dictionary (6th edition, 1995), published by The Cosmetic, Toiletry, and Fragrance Association, 1101 17th Street, N.W., Suite 300, Washington, DC 20036-4702.
Cosmetics & Toiletries Magazine, vol. 118, No. 8 (Aug. 2003) published by Allured Publishing Corp.
"DOW Corning 670 Fluid," Product Information: Personal Care, Ref. No. 27-1158-01 (2004).
Chinese Office Action for Application No. 200810142893.8 dated Jun. 25, 2013.
"Personal Care Applications for Silsesquioxane Resin Wax", IP.com Journal, IP.com Inc., West Henrietta, NY, US, Dec. 8, 2005, XP013112049.
Extended European Search Report for Application No. 08251967.9 dated Mar. 12, 2014.
Hidetoshi Kondo, "Cross-linked-Type Silicone Emulsifiers—Emulsifying Properties Thereof and Application Thereof in Cosmetics", Fragrance Journal, Jun. 2002, pp. 68 to 74.
Japanese Office Action for Application No. 2008-148499 dated Feb. 17, 2014.
Extended European Search Report for Application No. EP08251968 dated Mar. 18, 2014.
Mintel; Apr. 2007, "Mousse Foundation", XP002720910, Database accession No. 685829, Abstract.
Mintel, Apr. 2007, "Avon Glazewear Lipstick", <http:/gnpd.com>.
Third Party Observations for JP2013-243016 dated May 9, 2014.

* cited by examiner

COSMETIC COMPOSITIONS CONTAINING A PROPYLPHENYLSILSESQUIOXANE RESIN AND A COSMETICALLY-ACCEPTABLE AROMATIC SOLVENT

This application is based on and claims the benefit of U.S. Provisional Application Ser. No. 60/942,352, entitled COSMETIC COMPOSITIONS CONTAINING A PROPYLPHENYLSILSESQUIOXANE RESIN AND A COSMETICALLY-ACCEPTABLE AROMATIC SOLVENT, filed Jun. 6, 2007, the entire disclosure of which is incorporated by reference herein.

BACKGROUND OF THE INVENTION

Depending on the intended use, cosmetic compositions need to have several attributes. Wear, comfort of wear, adhesion and non transfer or transfer resistance are properties that are advantageous in most cosmetic compositions for the face, eye, lips nails or hair. Other properties, such as shine/gloss are not necessary in a foundation, blush or concealer, but may be actively sought in compositions for nails, lips or hair. Commercially available cosmetic compositions use combinations of ingredients which together impart one or more of the properties wanted by the consumer. Limiting the number of ingredients used in cosmetic compositions leads to manufacturing efficiencies while maintaining the desired properties. Currently, shine may be obtained through the addition of high refractive index fluids to further enhance the shine or gloss of such products, but the wear of shine or gloss is limited.

One problem associated with the use of known shine enhancing agents is that while they do tend to increase shine, the increased shine is extremely temporary. In other words, after a period of a few hours on the lips, the shine wears off and the user must reapply the lip shine composition in order to maintain shine.

Thus, it is one object of the present invention to provide a lip treatment composition capable of imparting a lasting shine onto the lips.

Another problem associated with the use of conventional shine enhancing agents is that they tend to make the lip treatment compositions tacky and uncomfortable to apply. This is due to the presence of high molecular weight polymers having a high viscosity which are used to slow the migration of the shiny oils.

Therefore, it is another object of the present invention to provide cosmetic compositions which are less tacky, more comfortable to apply and which exhibit lasting shine.

BRIEF SUMMARY OF THE INVENTION

A first aspect of the present invention is directed to a cosmetic composition containing: (a) at least one propylphenylsilsesquioxane resin comprising from up to about 80 mole % of propyl siloxy units, based on the total mole % of siloxy units of the resin, and from about 20 to about 100 mole % of phenyl siloxy units, based on the total mole % of siloxy units of the resin; (b) at least one cosmetically-acceptable aromatic solvent; (c) at least one colorant; and (d) optionally, at least one co-solvent having a molecular weight of from about 150 to about 10,000, and wherein the composition is substantially free of volatile solvents.

A second aspect of the present invention is directed to a method of imparting lasting shine/gloss onto lips comprising applying onto the lips the above-disclosed cosmetic composition.

DETAILED DESCRIPTION OF THE INVENTION

Other than in the operating examples, or where otherwise indicated, all numbers expressing quantities of ingredients and/or reaction conditions are to be understood as being modified in all instances by the term "about".

Propylphenylsilsesquioxane Resin

Silsesquioxane resins are a specific form of silicone resins. Silicone resins are crosslinked organopolysiloxanes which are solid at room temperature and generally soluble in organic solvents. When they are soluble in volatile solvents, silicone resins are capable of forming a film once the solvent has evaporated. Furthermore, if the solvent dissolving the silicone resin is absorbed on the substrate onto which it is applied, the silicone resin which remains on the substrate may also form a film.

The compositions of the present invention comprise propylphenylsilsesquioxane resins, which have been disclosed in patent publications WO2005/090444, published on Sep. 29, 2005; US20040180011, published on Sep. 16, 2004; and US20040156806, published on Aug. 12, 2004, the entire contents of each of which are hereby incorporated by reference.

The propylphenylsilsesquioxane resin comprises propyl siloxy units ($C_3H_7SiO_{3/2}$) and phenyl siloxy units ($C_6H_5SiO_{3/2}$). The propyl siloxy units comprise up to about 80 mole % of the total mole % of siloxy units of the resin, and the phenyl siloxy units comprise from about 20 to about 100 mole % of the total mole % of siloxy units of the resin.

The propylphenylsilsesquioxane resin will have a weight average molecular weight of from about 2,000 to about 30,000, such as from about 3,000 to about 20,000.

The propylphenylsilsesquioxane resins preferably soften in the range of from about 30° C. to about 100° C., such as from about 30° C. to about 80° C., and such as from about 40° C. to about 70° C., as determined by DIN 53180 "Softening Point of Resins".

The mole % of propyl siloxy units to phenyl siloxy units can be adjusted depending on an intended application. As such, it is possible to have propylphenylsilsesquioxane resins having a mole % propyl siloxy units:phenyl siloxy units ranging from about 80:20 to about 0:100, such as 70:30; 60:40; 50:50; 40:60; 30:70; 20:80; 10:90; 0:100; and subranges therebetween.

Suitable propylphenylsilsesquioxane resins include, but are not limited to, Belsil™ SPR 45, available from Wacker Chemical, Adrian, Mich.; DC217, available from Dow Corning, Midland, Mich.; DC Z-6018, a 30 mole % propyl and 70 mole % phenyl silsesquioxane, available from Dow Corning, Midland, Mich.

The mole % of phenyl siloxy units in the propylphenylsilsesquioxane resins can be chosen depending on the desired result. The higher the mole % of phenyl siloxy units, the shinier/glossier the composition is expected to be.

It should be noted that, in the event a phenylsilsesquioxane resin is used, it may be necessary to also use a propylphenylsilsesquioxane resin in order to plasticize the phenylsilsesquioxane resin.

The at least one propylphenylsilsesquioxane resin is generally present in the cosmetic composition of the invention in an amount ranging from about 5% to about 70% by weight; such as from about 10% to about 60% by weight; from about 15% to about 50% by weight; from about 20% to about 40% by weight, all weights based on the weight of the composition as a whole.

Cosmetically-Acceptable Aromatic Solvent

The compositions of the present invention comprise an aromatic solvent which is cosmetically acceptable.

The cosmetically acceptable aromatic solvent will comprise an aromatic portion in its molecule. Suitable cosmetically acceptable aromatic solvents include, but are not limited to, phenylated silicones, benzoate esters, benzyl esters, alkylated benzyl esters, alkylated benzyl ethers, and mixtures thereof. Preferred cosmetically acceptable aromatic solvents include, but are not limited to, trimethyl pentaphenyl trisiloxane available as DC555 from Dow Corning, C12-15 alkyl benzoate available as Finnsolv TN, PPG-3 benzyl ether myristate, available as Crodamol STS, PEG-2 benzyl ether available as Nikkol BZ-2, benzyl dodecanoate available as Pelemol 612, isostearyl benzoate available as Finsolv SB, phenethyl benzoate available as X-tend 226, 2-ethyl hexyl benzoate available as Finsolv EB, octyldodecyl benzoate available as Finsolv BOD, poly(propylene glycol)dibenzoates such as Dipropylene Glycol Dibenzoate, available as Finsolv PG-22.

The cosmetically acceptable aromatic solvent will typically be present in the cosmetic composition of the invention in an amount of from about 1% to about 95% by weight; such as from about 5% to about 80% by weight; such as from about 10% to about 70% by weight; such as from about 15% to about 60% by weight; such as from about 20% to about 50% by weight; such as from about 25% to about 40% by weight, all weights based on the weight of the composition as a whole.

Colorant

The cosmetic compositions of the present invention will also contain at least one cosmetically acceptable colorant such as a pigment or dyestuff. Examples of suitable pigments include, but are not limited to, inorganic pigments, organic pigments, lakes, pearlescent pigments, irridescent or optically variable pigments, and mixtures thereof. A pigment should be understood to mean inorganic or organic, white or colored particles. The pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on Cochineal Carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the compositions of the present invention will depend on the color, intensity and use of the cosmetic composition and, as a result, will be determined by those skilled in the art of cosmetic formulation.

The present composition is substantially free of volatile solvents. By "substantially free", it is meant that volatile solvent is present in the composition of the invention, in an amount of less than about 3% by weight, based on the weight of the composition as a whole.

The volatile solvent, if present in an amount of less than about 3% by weight, may be a volatile silicone solvent and/or a volatile non-silicone solvent. Preferably, the volatile solvent has a flash point of at least 40° C. Examples of volatile silicone solvents present in an amount of less than about 3% by weight include, but are not limited to, linear or cyclic silicone oils having a viscosity at room temperature less than or equal to 6 cSt and having from 2 to 7 silicon atoms, such as cyclomethicone and dimethicone. Examples of volatile non-silicone solvents present in an amount of less than about 3% by weight, include but are not limited to, volatile hydrocarbon oils, alcohols, volatile esters and volatile ethers, such as $C_8$ to $C_{16}$ isoparaffins, isododecane, the oils sold under the trade names of Isopar or Permethyl, the $C_8$ to $C_{16}$ branched esters such as isohexyl or isodecyl neopentanoate and their mixtures Additives/Auxiliary Agents The composition of the present invention may contain additional additives or auxiliary agents in order to provide additional cosmetic benefits and/or to facilitate various physical forms of said composition.

Co-Solvent

In an effort to improve the flow and leveling of the cosmetic composition during application onto the lips, as well as its feel and comfort thereon, it may be desirable to further include a co-solvent in the cosmetic composition.

The co-solvents which may be used will typically have a weight average molecular weight in the range of about 150 to about 10,000, such as from about 200 to about 5,000, such as from about 250 to about 2,500.

Nonvolatile co-solvents which may be used in the invention include, but are not limited to, monoesters, diesters, triesters, mixed aliphatic and/or aromatic, polar oils such as: hydrocarbon-based oils of animal origin, such as perhydrosqualene; hydrocarbon-based plant oils such as liquid triglycerides of fatty acids and of glycerol, in which the fatty acids may have varied chain lengths, these chains being linear or branched, and saturated or unsaturated; these oils can be chosen, for example, from wheat germ oil, sunflower oil, corn oil, soybean oil, marrow oil, grapeseed oil, blackcurrant seed oil, sesame oil, hazelnut oil, apricot oil, macadamia oil, castor oil, avocado oil, karite butter, sweet almond oil, cotton oil, alfalfa oil, poppy oil, pumpkin oil, evening primrose oil, millet oil, barley oil, quinoa oil, olive oil, rye oil, safflower oil, candlenut oil, passion flower oil, musk rose oil and caprylic/capric acid triglycerides such as those sold by the company Stéarineries Dubois or those sold under the names Miglyol® 810, 812 and 818 by the company Dynamit Nobel; natural or synthetic esters of formula $R_1COOR_2$, wherein $R_1$ is a higher fatty acid residue comprising 7 to 19 carbon atoms, and $R_2$ is a branched hydrocarbon-based chain comprising 3 to 20 carbon atoms, such as, for example, purcellin oil (cetostearyl octanoate), isopropyl myristate and alkyl or polyalkyl octanoates, decanoates or ricinoleates; synthetic ethers of formula $R^aCOR^b$, wherein $R^a$ is a $C_5$ to $C_{19}$ alkyl radical, and $R^b$ is a $C_5$ to $C_{20}$ alkyl radical; fatty alcohols comprising at least 12 carbon atoms, such as octyldodecanol or oleyl alcohol; cyclic hydrocarbons such as (alkyl)cycloalkanes, wherein the alkyl chain is linear or branched, saturated or unsaturated and comprises 1 to 30 carbon atoms, such as cyclohexane or dioctylcyclohexane; primary, secondary or tertiary amines such as triethanolamine; liquid phenylsilsesquioxanes such as those described in US2003077240 A1, the entire content of which is hereby incorporated by reference; and mixtures thereof.

Suitable co-solvents further include, but are not limited to, isopropyl myristate (Mw=270), isopropyl palmitate (Mw=300), isononyl isononanoate, cetyl ethylhexanoate (Mw=368), neopentyl glycol diethylhexanoate (Mw=356), diisopropyl sebacate (Mw=286), capric/caprylic triglyceride (Mw=500), diisopropyl dimer dilinoleate (Mw=644), diisostearyl fumarate (Mw=620), diisostearyl malate (Mw=640).

Esters such as pentaerythrityl tetraoleate, neopentyl glycol diethylhexanoate, diethylhexyl sebacate and tricaprylate/tricaprate may also be used.

Examples of additional co-solvents may include, but are not limited to, the aminopropyl phenyl trimethicone commercialized under the trade name "DC2-2078®" by Dow Corning, phenylated silicones such as those commercialized under the trade name "Abil AV 8853®" by Goldschmidt, those commercialized under the trade names "DC 554®", "DC 556®", by Dow Corning, those commercialized under the trade name "SF 558®" by GE Silicones, those commercialized under the trade name "Silbione 70633V 30®" by Rhône-Poulenc, those commercialized under the trade name Belsil, such as PDM 20®, a phenylated silicone with a viscosity at 25° C. of approximately 20 cSt; Belsil PDM 200®, a phenylated silicone with a viscosity at 25° C. of approximately 200 cSt; Belsil PDM 1000®, a phenylated silicone with a viscosity at 25° C. of approximately 1000 cSt (Belsil® is a registered trade name of the Wacker Chemical company.) The at least one co-solvent may typically be present in the cosmetic composition of the invention in an amount from about 1% to about 70% by weight; such as from about 5% to about 60%; such as from about 15% to about 40% by weight, all weights based on the weight of the composition as a whole.

Modified Silicones

The cosmetic compositions of the present invention may contain at least one modified silicone to improve the texture and comfort. Examples of suitable modified silicones include, but are not limited to, polyethyleneoxy- and/or polypropyleneoxy-modified silicone, alkoxy-modified silicone, hydroxyalkyl-modified silicone, acyloxyalkyl-modified silicone, alkyl-modified silicone, amino-modified silicone, epoxy-modified silicone, carboxyl-modified silicone, chloroalkyl-modified silicone, alkyl-higher-alcohol-ester-modified silicone, alcohol-modified silicone, polyether-modified silicone, alkylpolyglyceryl-modified silicone, perfluoroalkyl polyether-co-modified silicone and fluorine-modified silicone.

The modified silicone may be present in the cosmetic composition of the invention in an amount of up to about 30% by weight; such as up to about 25% by weight; such as up to about 20% by weight; such as up to about 10% by weight; such as up to about 8% by weight, all weights based on the weight of the composition as a whole.

Waxes/Structuring Agents

In some embodiments, it may be desirable to formulate cosmetic compositions which are thick or which do not flow at room temperature. This can be accomplished with the use of structuring agents which can be waxes and/or other structuring agents. It may also be desirable to formulate structured compositions in accordance with the present invention which are free of wax.

In the event a wax is employed, waxes suitable for use in the composition of the present invention are those generally used in cosmetics and dermatology. Examples thereof include, but are not limited to, those of natural origin such as beeswax, carnauba wax, candelilla wax, ouricury wax, Japan wax, cork fiber wax, sugar cane wax, paraffin wax, lignite wax, microcrystalline waxes, lanolin wax, montan wax, ozokerites and hydrogenated oils such as hydrogenated jojoba oil. Examples of suitable synthetic waxes include, but are not limited to, polyethylene waxes derived from the polymerization of ethylene; waxes obtained by Fischer-Tropsch synthesis; fatty acid esters and glycerides that are solid at 40° C., for example, at above 55° C.; silicone waxes such as alkyl- and alkoxy-poly(di)methylsiloxanes; and/or poly(di)methyl-siloxane esters that are solid at above 40° C., for example, at above 55° C.

Structuring agents may also include, but are not limited to:

(A) non-silicone based polyamides such as those known in the trade as Uniclear® or Sylvaclear®. These non silicone polyamides have different terminal end groups, such as ester terminated, known as Uniclear® 80 or 100, such as amide terminated, known as Sylvaclear® A200, and such as polyalkyleneoxy terminated, known as Sylvaclear® AF1900, as well as ester terminated polyesteramides. These non silicone polyamides are available, for instance, from Arizona Chemical Company, Jacksonville, Fla., and are described in U.S. Pat. No. 5,783,657, U.S. Pat. No. 6,402,408, U.S. Pat. No. 6,268,466, U.S. Pat. No. 6,552,160 the entire contents of which are incorporated by reference;

(B) silicone-based polyamide resins such as those described in US patent application published as US2006/0120983 A1, the entire content of which is hereby incorporated by reference.

The structuring agents may be present in the cosmetic composition of the invention in an amount of from about 0.1% to about 30% by weight, based on the total weight of the composition as a whole.

Gelling Agents

The compositions of the invention may also be optionally gelled with at least one gelling agent. The gelling agent increases the liquid fatty phase viscosity and leads to a solid or flowable composition when introduced in said fatty phase. The gelling agent does not encompass waxes, in the sense that it is not waxy. The at least one gelling agent may be chosen from gelling agents in polymeric form and gelling agents in mineral form. The gelling agent may be chosen from agents that gel via chemical reticulation and agents that gel via physical reticulation.

Modified clays may be used as gelling agents, examples of which include, but are not limited to, hectorites modified with an ammonium chloride of a $C_{10}$ to $C_{22}$ fatty acid, such as hectorite modified with distearyldimethylammonium chloride, also known as quaternium-18 bentonite, such as the products sold or made under the names "Bentone 34®" by the company Rheox, "Claytone XL®", "Claytone 34®" and "Claytone 40®" sold or made by the company Southern Clay, the modified clays known under the name quaternium-18 benzalkonium bentonites and sold or made under the names "Claytone HT®", "Claytone GR®" and "Claytone PS®" by the company Southern Clay, the clays modified with stearyldimethylbenzoylammonium chloride, known as stearalkonium bentonites, such as the products sold or made under the names "Claytone APA®" and "Claytone AF®" by the company Southern Clay, and "Baragel 24®" sold or made by the company Rheox.

Other mineral gelling agents, which can be used in the invention, include silica, such as fumed silica. The fumed silica may have a particle size, which may be nanometric to micrometric, for example ranging from about 5 nm to about 200 nm.

The fumed silicas may be obtained by high-temperature hydrolysis of a volatile silicon compound in a hydrogen-oxygen flame, producing a finely divided silica. This process makes it possible to obtain hydrophilic silicas that have a large number of silanol groups at their surface. Such hydrophilic silicas are sold or made, for example, under the names "Aerosil 130®", "Aerosil 200®", "Aerosil 255®", "Aerosil 300®" and "Aerosil 380®" by the company Degussa, and "CAB-O-SIL HS-5®", "CAB-O-SIL EH-5®", "CAB-O-SIL LM-130®", "CAB-O-SIL MS-55®" and "CAB-O-SIL M-5®" by the company Cabot.

It is thus possible to chemically modify the surface of the hydrophilic silica by chemical reaction, producing a reduction in the number of silanol groups. The silanol groups can be replaced, for example, with hydrophobic groups: this then gives a hydrophobic silica. The hydrophobic groups may be: trimethylsiloxyl groups, which are obtained in particular by treating fumed silica in the presence of hexamethyldisilazane. Silicas thus treated are known as "silica silylate" according to the CTFA dictionary (6th edition, 1995). They are sold or made, for example, under the references "Aerosil R812®" by the company Degussa and "CAB-O-SIL TS-530®" by the company Cabot; dimethylsilyloxyl or polydimethylsiloxane groups, which are obtained in particular by treating fumed silica in the presence of polydimethylsiloxane or dimethyldichlorosilane. Silicas thus treated are known as "silica dimethyl silylate" according to the CTFA dictionary (6th edition, 1995). They are sold or made, for example, under the references "Aerosil R972®" and "Aerosil R974®" by the company Degussa, and "CAB-O-SIL TS-610®" and "CAB-O-SIL TS-720®" by the company Cabot; groups derived from reacting fumed silica with silane alkoxides or siloxanes. These treated silicas are, for example, the products sold or made under the reference "Aerosil R805®" by the company Degussa.

According to the invention, hydrophobic silica, such as fumed silica, may be used as a lipophilic gelling agent. The use of fumed silica makes it possible to obtain a translucent or even transparent composition, in particular in the form of a stick, which does not exude, in the absence of opacifying particles such as waxes, fillers and pigments (including nacres).

The at least one lipophilic gelling agent can allow the exudation of the composition to be limited and can allow its stability to be increased, while at the same time conserving the composition's glossy appearance, which is not possible with waxes such as those used conventionally in cosmetics and dermatology.

The at least one gelling agent, if used, will typically be present in the cosmetic composition of the invention in an amount of from about 0.1% to about 20% by weight, such as from about 0.1% to about 15% by weight, and such as from about 0.1 to about 10% by weight, all weights based on the weight of the composition as a whole.

The compositions of the present invention may also further comprise other cosmetically or dermatologically acceptable additives such as a thickener, a film former, a plasticizer, an antioxidant, a surfactant, an essential oil, a preserving agent, a fragrance, a filler, a pasty fatty substance, a waxy fatty substance, a neutralizing agent, and a polymer, and cosmetically active agents and/or dermatological active agents such as, for example, emollients, moisturizers, vitamins, essential fatty acids and medicaments.

Additional film formers may be also used in the composition of the present invention. Film formers are also known as film-forming polymers. The term "film-forming polymer" is understood to mean a polymer capable of forming, alone and/or in the presence of a plasticizer, an isolable film. The film-forming polymer can be dissolved or dispersed in the form of particles in the solvent of the composition.

Suitable film-formers can be chosen from radical polymers, polycondensates and polymers of natural origin. Such cosmetically acceptable film formers may be found in the International Cosmetic Ingredient Dictionary and Handbook, $9^{th}$ edition, 2002 pages 2903-2906.

Suitable film-forming polymers include, but are not limited to, vinyl and acrylic polymers, polyurethanes, polyesters, alkyd resins, epoxy ester resins, cellulose polymers, such as nitrocellulose, cellulose esters, such as cellulose acetate, cellulose acetate propionate or cellulose acetate butyrate, resins resulting from the condensation of formaldehyde with an arylsulphonamide, and their mixtures. Furthermore, film formers may include silicone resins other than the silsesquioxanes, such as trimethylsiloxysilicates.

While the use of a plasticizer is not necessary in the cosmetic composition of the present invention, its use may, nevertheless, be desirable. Plasticizers are organic compounds added to a high polymer both to facilitate processing and to increase the flexibility and toughness of the final product by internal modification of the polymer molecule. Examples of suitable plasticizers include, but are not limited to, oils, cellulose esters, phthalate esters, adipate esters, sebacate esters, tricresyl phosphate, castor oil, glycol ethers, benzyl alcohol, triethyl citrate, and propylene carbonate.

A plasticizer, if used, will typically be present in the cosmetic composition of the invention in an amount of from about 1% to about 70% by weight, such as from about 2% to about 50% by weight, and such as from about 5% to about 20% by weight, all weights based on the weight of the composition as a whole.

The composition of the invention may be in the form of an emulsion which may contain surfactants or a mixture thereof. Suitable surfactants for use in a composition of the present invention in the form of an emulsion include anionic, non-ionic, amphoteric and cationic surfactants. See, e.g., Encyclopedia of Chemical Technology, KIRK-OTHMER, volume 22, pp. 333-432, 3rd edition, 1979, Wiley, for the definition of the properties and (emulsifying) functions of the surfactants, in particular pp. 347-377 of this publication regarding anionic and nonionic surfactants.

Suitable anionic surfactants useful in the compositions of the invention may include, but are not limited to, $C_{16}$-$C_{30}$ fatty acids neutralized by amines, ammonia or the alkali metal salts thereof.

Suitable nonionic surfactants useful in the compositions of the invention may include, but are not limited to, fatty acids, fatty alcohols, polyethoxylated fatty alcohols or polyglycerolated fatty alcohols, such as polyethoxylated stearyl alcohols or cetylstearyl alcohols, esters of fatty acid and sucrose, and glucose alkyl esters, in particular polyoxyethylenated $C_1$-$C_6$ alkyl glucose fatty esters.

Suitable amphoteric surfactants may include, but are not limited to, betaines, sultaines, hydroxysultaines, alkyl amphodiacetates, alkyl amphodipropionates, and imidazolines, or salts thereof. Other fatty acid condensates such as those formed with amino acids, proteins, and the like are suitable as well. Specific examples may include cocoamphodipropionate, e.g., "Miranol C2M-SF®" (disodium cocoamphodipropionate), in its salt-free form, available from Rhône-Poulenc, and "Crosultaine C-50®" (cocamidopropyl hydroxysultaine), available from Croda.

Suitable cationic surfactants may include, but are not limited to, quaternary amines, amine oxides and amines, e.g., alkyl amines, alkyl imidazolines, ethoxylated amines, quaternary compounds, and quaternized esters.

Surfactants may be present in the cosmetic composition of the invention in an amount ranging from about 1% to about 30% by weight, such as from about 5% to about 15% by weight, all weights based on the weight of the composition as a whole.

Suitable preservatives in the composition of the present invention may include, but not limited to, phenoxyethanol, alkyl para-hydroxybenzoates, wherein the alkyl radical has from 1, 2, 3, 4, 5 or 6 carbon atoms and preferably from 1 to 4 carbon atoms e.g., methyl para-hydroxybenzoate(methylparaben), ethyl para-hydroxybenzoate(ethylparaben), propyl para-hydroxybenzoate(propylparaben), butyl para-hydroxybenzoate(butylparaben), isobutyl para-hydroxybenzoate(isobutylparaben), and their mixtures.

The preservatives may be present in the cosmetic composition of the invention in an amount ranging from about 0.01% to about 10% by weight, such as from 0.5% to about 5% by weight, and such as from about 0.8% to about 3% by weight, all weights based on the weight of the composition as a whole.

Suitable fillers in the composition include, but are not limited to, silica powder; talc; polyamide particles such as those sold under the name Orgasol® by the company Atochem; polyethylene powders; microspheres based on acrylic copolymers, such as those sold under the name Polytrap® by the company Dow Corning; expanded powders such as hollow microspheres such as those sold under the name Expancel® by the company Kemanord Plast, or under the name "Micropearl F 80 ED®" by the company Matsumoto; powders of natural organic materials such as crosslinked or noncrosslinked corn starch, wheat starch or rice starch, such as the powders of starch crosslinked with octenyl succinate anhydride, sold under the name Dry-Flo® by the company National Starch; silicone resin microbeads such as those sold under the name Tospearl® by the company Toshiba Silicone; clays (bentone, laponite, saponite, etc.) and mixtures thereof.

The fillers may be present in the composition of the invention in an amount ranging from about 0.1% to about 50% by weight, such as from 0.5% to about 30% by weight, and such as from about 1% to about 20% by weight, all weights based on the weight of the composition as a whole.

According to one embodiment of the invention, the cosmetic composition of the present invention may further contain a high viscosity ester, such as sucrose acetate isobutyrate which may be added for improvement of wear and shine properties. A suitable sucrose acetate isobutyrate compound includes "SAIB-100®", available from Eastman, Kingsport, Tenn. It has a viscosity of about 100,000 cps at 30° C., and a refractive index of about 1.5 at 20° C.

The sucrose acetate isobutyrate may be present in the composition of the invention in an amount ranging from about 1% to about 20% by weight, such as from 2% to about 15% by weight, and such as from about 3% to about 10% by weight, all weights based on the weight of the composition as a whole.

The composition of the present invention may further comprise a safe and effective amount of at least one active ingredient or pharmaceutically acceptable salt thereof. The term "safe and effective amount" as used herein, means an amount sufficient to modify the condition to be treated or to deliver the desired skin benefit, while at the same time avoiding serious side effects, at a reasonable benefit to risk ratio within the scope of sound medical judgment. The safe and effective amount of the active ingredient will vary with the specific active agent, the ability of the active agent to penetrate through the skin, the age, health and skin condition of the user, and other like factors. Typically, the active ingredient may be present in the composition of the invention in an amount ranging from about 0.01% to about 20% by weight, such as from 0.1% to about 10% by weight, and such as from about 0.5% to about 5% by weight, all weights based on the weight of the composition as a whole.

The active ingredients useful herein can be categorized by their therapeutic benefit or their postulated mode of action. However, it is to be understood that the active ingredients useful herein can in some instances provide more than one therapeutic benefit or operate via more than one mode of action. Therefore, classifications herein are made for the sake of convenience and are not intended to limit the active ingredient to that particular application or applications listed. Also, pharmaceutically acceptable salts of these active ingredients are useful herein. The following active ingredients are useful in the compositions of the present invention.

Antimicrobial and Antifungal Actives: Examples of antimicrobial and antifungal actives include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate and clotrimazole.

The cosmetic composition of the present invention may also contain sunscreens, which are chemical absorbers that actually absorb harmful ultraviolet radiation. It is well known that chemical absorbers are classified, depending on the type of radiation they protect against, as either UV-A or UV-B absorbers. UV-A absorbers generally absorb radiation in the 320 to 400 nm region of the ultraviolet spectrum. UV-A absorbers include anthranilates, benzophenones, and dibenzoyl methanes. UV-B absorbers generally absorb radiation in the 280 to 320 nm region of the ultraviolet spectrum. UV-B absorbers include p-aminobenzoic acid derivatives, camphor derivatives, cinnamates, and salicylates.

The sunscreens useful in the cosmetic composition of the present invention typically comprise chemical absorbers, but may also comprise physical blockers. Exemplary sunscreens which may be formulated into the compositions of the present invention are chemical absorbers such as p-aminobenzoic acid derivatives, anthranilates, benzophenones, camphor derivatives, cinnamic derivatives, dibenzoyl methanes (such as avobenzone also known as Parsol® 1789), diphenylacrylate derivatives, salicylic derivatives, triazine derivatives, benzimidazole compounds, bis-benzoazolyl derivatives, methylene bis-(hydroxyphenylbenzotriazole) compounds, the sunscreen polymers and silicones, or mixtures thereof. Also exemplary of the sunscreens which may be formulated into the compositions of this invention are physical blockers such as cerium oxides, chromium oxides, cobalt oxides, iron oxides, red petrolatum, silicone-treated titanium dioxide, titanium dioxide, zinc oxide, and/or zirconium oxide, or mixtures thereof.

Examples of suitable sunscreens include, but are not limited to: aminobenzoic acid, amyldimethyl PABA, cinoxate, diethanolamine p-methoxycinnamate, digalloyl trioleate, dioxybenzone, 2-ethoxyethyl p-methoxycinnamate, ethyl 4-bis(hydroxypropyl)aminobenzoate, 2-ethylhexyl-2-cyano-3,3-diphenylacrylate, ethylhexyl p-methoxycinnamate, 2-ethylhexyl salicylate, glyceryl aminobenzoate, homomethyl salicylate, homosalate, 3-imidazol-4-ylacrylic acid and ethyl ester, methyl anthranilate, octyldimethyl PABA, 2-phenylbenzimidazole-5-sulfonic acid and salts, red petrolatum, sulisobenzone, titanium dioxide, triethanolamine salicylate, N,N,N-trimethyl-4-(2-oxoborn-3-ylidene methyl)anillinium methyl sulfate, and mixtures thereof.

The sunscreens may be present in the composition of the invention in an amount of from greater than about 0 to about 30% by weight, based on the weight of the composition as a whole.

The composition of the present invention has particular usefulness as a solid lipstick product intended to provide long lasting shine/gloss.

EXAMPLE

The present invention is further described in terms of the following non-limiting examples. Unless otherwise indicated, all parts and percentages are on a weight-by-weight percentage basis.

Examples 1, and 2 (Inventive Compositions)

Solid Lipsticks

| Phase | Ingredient | Ex. 1 % w/w | Ex. 2 % w/w |
|---|---|---|---|
| A | Wacker SPR 45 VP | 20.00 | 0 |
|  | DC Z-6018 | 0 | 10.00 |
|  | C12-15 alkyl benzoate (Finsolv TN) | 10.15 | 10.15 |
|  | Trimethyl pentaphenyl trisiloxane (DC555) | 39.00 | 59.00 |
| B | Sucrose acetate isobutyrate | 10.00 | 0 |
| C | Pigments | 3.85 | 3.85 |
|  | Diisopropyl dimer dilinoleate | 5.00 | 5.00 |
| D | Beeswax | 4.00 | 4.00 |
|  | Ozokerite | 7.00 | 7.00 |
|  | Polymethylsilsesquioxane beads (Tospearl) | 1.00 | 1.00 |
|  | Total | 100.00 | 100.00 |

Examples 3 and 4 (Comparative Compositions)

Solid Lipsticks

| Phase | Ingredient | Ex. 3 % w/w | Ex. 4 % w/w |
|---|---|---|---|
| A | Wacker SPR 45 VP | 20.00 | 20.00 |
|  | C12-15 alkyl benzoate (Finsolv TN) | 4.00 | 5.00 |
|  | Trimethyl pentaphenyl trisiloxane (DC555) | 39.00 | 34.00 |
| B | Sucrose acetate isobutyrate | 0 | 8.00 |
|  | Bis-diglyceryl polyacyladipate-2 (Softisan 649) | 4.00 | 4.00 |
|  | Octyldodecyl neopentanoate | 7.15 | 3.15 |
|  | Isododecane | 5.00 | 4.00 |
| C | Pigments | 3.85 | 3.85 |
|  | Diisopropyl dimer dilinoleate | 5.00 | 5.00 |
| D | Beeswax | 4.00 | 4.00 |
|  | Ozokerite | 7.00 | 7.00 |
|  | Polymethylsilsesquioxane beads (Tospearl) | 1.00 | 2.00 |
|  | Total | 100.00 | 100.00 |

Shine Measurement Protocol

In order to measure the shine of the above-mentioned cosmetic product, the intensity of the light used to perform the measurement was first determined and then its reflection off the surface of the lips was measured. This was done by having a first polarizer with vertical orientation in front of the light source, and a second polarizer with vertical orientation in front of a video camera. The video camera, with the rotating polarizer oriented vertically; i.e., in the same direction as the source light polarizers, first recorded the surface reflection along with vertical light remitted from the gloss and/or the lip.

The polarizer in front of the camera was then rotated by 90 degrees (at a video rate) in order to record the intensity of any vertical light remitted from below the surface. The horizontal intensity of sub-surface transmitted light was then measured. The second, horizontal measurement was a correction accounting for any sub-surface contributions to the desired surface signal (the gloss). The second number was then subtracted from the first to yield the shine value.

A more detailed explanation of the process and method used to evaluate the shine value of a cosmetic composition is found in U.S. Pat. No. 7,127,280, the entire content of which is hereby incorporated by reference.

Shine Kinetics Table

Shine values for inventive examples 1 and 2, and comparative examples 3 and 4.

|  | Ex. 1 | Ex. 2 | Ex. 3 | Ex. 4 |
|---|---|---|---|---|
| T0 | 159 ± 12 | 166 ± 9 | 138 ± 18 | 177 ± 12 |
| T1 hr | 156 ± 14 | 166 ± 12 | 143 ± 16 | 173 ± 13 |
| T2 hr | 158 ± 17 | 160 ± 12 | 127 ± 18 | 159 ± 21 |

The results demonstrate that the shine provided by the inventive formulations is long lasting.

As can be seen from the above data, the compositions exhibiting long lasting shine, such as examples 1 and 2, show a drop in shine value of less than 10; in other words, after a period of two hours following application, the change in shine value as compared to the initial value is 10 or less. Conversely, as observed in examples 3 and 4, the reduction in shine value is greater than 10 which equates to a perceivable reduction in shine when viewed by the naked eye.

Preparation Procedure

Phase A ingredients were mixed together into a beaker, which was then transferred to a 90° C. oil bath and mixed with a propeller mixer. Mixing was continued until the system was uniform. Phase B ingredients were mixed together and added to Phase A. Phase C ingredients were mixed together and the resulting mixture was transferred to a three-roll Mill and milled 4 times. The color grind mixture was then transferred into the beaker containing Phase A+B. Then, Phase D ingredients were added to A+B+C and mixed at 100° C. until the waxes have melted and the mixture was uniform. The resulting fluid was transferred to a mold and put in a freezer for 30 minutes. The resulting stick was then transferred into individual packages.

It is to be understood that the foregoing describes preferred embodiments of the invention and that modifications may be made therein without departing from the spirit or scope of the invention as set forth in the claims.

What is claimed is:

1. A cosmetic composition comprising:
    (a) at least one silsesquioxane resin chosen from a propylphenylsilsesquioxane resin having a weight average molecular weight of from about 2,000 to about 30,000, wherein the propylphenylsilsesquioxane resin comprises propyl siloxy units ($C_3H_7SiO_{3/2}$) and phenyl siloxy units ($C_6H_5SiO_{3/2}$), and wherein the propyl siloxy units comprise from greater than 0% up to about 80 mole % of the total mole % of siloxy units of the resin, and the phenyl siloxy units comprise from about 20 to about less than 100 mole % of the total mole % of siloxy units of the resin, and a phenylsilsesquioxane resin having a molecular weight of from about 2,000 to about 30,000;
    (b) at least one cosmetically acceptable aromatic solvent consisting of C12-15 alkyl benzoate, PPG-3 benzyl ether myristate, or a mixture thereof;
    (c) at least one colorant; and
    (d) optionally sucrose acetate isobutyrate; and
    wherein the composition is substantially free of volatile solvents.

2. The composition of claim 1, wherein (a) is a propylphenylsilsesquioxane having a weight average molecular weight of about 3,000 to about 20,000.

3. The composition of claim 1, wherein (a) is a phenylsilsesquioxane.

4. The composition of claim 1, wherein (a) is present in an amount of from about 5% to about 70% by weight, based on the weight of the composition as a whole.

5. The composition of claim 1, wherein (a) is present in an amount of from about 10% to about 60% by weight, based on the weight of the composition as a whole.

6. The composition of claim 1, wherein (a) comprises about 30 mole % propyl siloxy units and about 70 mole % phenyl siloxy units, based on the total mole % of the siloxy units of (a).

7. The composition of claim 1, wherein (b) is C12-15 alkyl benzoate.

8. The composition of claim 1, wherein (b) is PPG-3 benzyl ether myristate.

9. The composition of claim 1, wherein (b) is present in an amount of from about 1% to about 95% by weight, based on the weight of the composition as a whole.

10. The composition of claim 1, wherein (b) present in an amount of from about 5% to about 80%, based on the weight of the composition as a whole.

11. The composition of claim 1, wherein the composition is in solid form.

12. The composition of claim 1, further comprising the sucrose acetate isobutyrate.

13. The composition of claim 12, wherein the sucrose acetate isobutyrate has a viscosity of about 100,000 cps at 30° C., and a refractive index of about 1.5 at 20° C.

14. The composition of claim 12, wherein the sucrose acetate isobutyrate is present in an amount of from about 1 to about 20% by weight, based on the weight of the composition as a whole.

15. A method of imparting lasting shine onto lips comprising applying to the lips a cosmetic composition containing:
    (a) at least one silsesquioxane resin chosen from a propylphenylsilsesquioxane resin having a weight average molecular weight of from about 2,000 to about 30,000, wherein the propylphenylsilsesquioxane resin comprises propyl siloxy units ($C_3H_7SiO_{3/2}$) and phenyl siloxy units ($C_6H_5SiO_{3/2}$), and wherein the propyl siloxy units comprise from greater than 0% up to about 80 mole % of the total mole % of siloxy units of the resin, and the phenyl siloxy units comprise from about 20 to about less than 100 mole % of the total mole % of siloxy units of the resin, and a phenylsilsesquioxane resin having a molecular weight of from about 2,000 to about 30,000;
    (b) at least one cosmetically acceptable aromatic solvent consisting of C12-15 alkyl benzoate, PPG-3 benzyl ether myristate, or a mixture thereof;
    (c) at least one colorant; and
    (d) optionally sucrose acetate isobutyrate; and
    wherein the composition is substantially free of volatile solvents.

16. The method of claim 15, wherein (a) is a propylphenylsilsesquioxane having a weight average molecular weight of about 3,000 to about 20,000.

17. The method of claim 15, wherein (a) is a phenylsilsesquioxane.

18. The method of claim 15, wherein (a) is present in an amount of from about 5% to about 70% by weight, based on the weight of the composition as a whole.

19. The method of claim 15, wherein (a) is present in an amount of from about 10% to about 60% by weight, based on the weight of the composition as a whole.

20. The method of claim 15, wherein (a) comprises about 30 mole % propyl siloxy units and about 70 mole % phenyl siloxy units, based on the total mole % of the siloxy units of (a).

21. The method of claim 15, wherein (b) is C12-15 alkyl benzoate.

22. The method of claim 15, wherein (b) is PPG-3 benzyl ether myristate.

23. The method of claim 15, wherein (b) is present in an amount of from about 1% to about 95% by weight, based on the weight of the composition as a whole.

24. The method of claim 15, wherein (b) present in an amount of from about 5% to about 80%, based on the weight of the composition as a whole.

25. The method of claim 15, wherein the composition is in solid form.

26. The method of claim 15, wherein the composition further comprises the sucrose acetate isobutyrate.

27. The method of claim 26, wherein the sucrose acetate isobutyrate has a viscosity of about 100,000 cps at 30° C., and a refractive index of about 1.5 at 20° C.

28. The method of claim 26, wherein the sucrose acetate isobutyrate is present in an amount of from about 1 to about 20% by weight, based on the weight of the composition as a whole.

* * * * *